(12) United States Patent
Wedell et al.

(10) Patent No.: US 7,598,076 B2
(45) Date of Patent: Oct. 6, 2009

(54) CELL CULTURE INSERT

(75) Inventors: Gabriele Wedell, Goppeln (DE);
Helmut Matthes, Grosserkmannsdorf (DE)

(73) Assignee: Oxyphen AG, Zug (CH)

( * ) Notice: Subject to any disclaimer, the term of this patent is extended or adjusted under 35 U.S.C. 154(b) by 874 days.

(21) Appl. No.: 10/522,544

(22) PCT Filed: Aug. 1, 2003

(86) PCT No.: PCT/EP03/08527

§ 371 (c)(1),
(2), (4) Date: Jan. 27, 2005

(87) PCT Pub. No.: WO2004/020571

PCT Pub. Date: Mar. 11, 2004

(65) Prior Publication Data

US 2006/0051857 A1 Mar. 9, 2006

(30) Foreign Application Priority Data

Aug. 30, 2002 (DE) ................. 102 40 787

(51) Int. Cl.
*C12M 1/12* (2006.01)
(52) U.S. Cl. .................................... 435/297.5
(58) Field of Classification Search ............... 435/297.5
See application file for complete search history.

(56) References Cited

U.S. PATENT DOCUMENTS

| 4,871,674 | A | | 10/1989 | Matsui et al. |
| 5,272,083 | A | | 12/1993 | Butz et al. |
| 5,366,893 | A | * | 11/1994 | Stevens et al. ........... 435/297.5 |
| 5,534,227 | A | | 7/1996 | Lahm et al. |
| 5,578,492 | A | | 11/1996 | Fedun |
| 5,652,142 | A | * | 7/1997 | Barker et al. ............. 435/297.1 |
| 5,710,043 | A | * | 1/1998 | Pay ......................... 435/297.5 |

FOREIGN PATENT DOCUMENTS

| EP | 0 590 513 A1 | 4/1994 |
| WO | WO 92/07063 A2 | 4/1992 |

\* cited by examiner

*Primary Examiner*—Walter D Griffin
*Assistant Examiner*—Lydia Edwards
(74) *Attorney, Agent, or Firm*—Browdy and Neimark, P.L.L.C.

(57) ABSTRACT

The invention relates to a cell culture insert (1) comprising a beaker-shaped insert wall (11), a base (9) consisting of a membrane filter, projecting support arms (3, 4) that are distributed around the periphery of the top and lateral spacers (7, 8) for a vertical and horizontal orientation in a well (2) containing a liquid culture medium (N) in a cell culture plate. According to the invention, the spacers (7, 8) are distributed around the periphery of the cell culture insert (1) and have different radial lengths in such a way that a large feed opening (5) and several smaller openings (5A) are formed.

16 Claims, 4 Drawing Sheets

CELL CULTURE INSERT

The invention relates to a cell culture insert comprising a beaker-shaped insert wall having a membrane filter bottom and projecting support arms that are distributed around the circumference of the top and having lateral spacers for a vertical and horizontal orientation in a well with a liquid culture medium in a cell culture plate.

Cell culture inserts, in order to be easy to work with, should have a large feed opening. Also, the lower cross section with the membrane should be sufficiently large to permit a good fluid exchange between the beaker content and well content. It is also advantageous to suspend the cell culture inserts in the well in order not to have any feet at the lower edge of the insert that interfere with the cell growth. In addition to the accessibility of the cell culture insert through the feed opening, the accessibility of the well bottom for pipets is also important.

Cell culture inserts in beaker shape are known, from patent document U.S. Pat. No. 4,871,674 and U.S. Pat. No. 5,578,492 for example, which are suspended in a well and permit access to the cell culture insert and to the well. The cell inserts that are described here are constructed symmetrically and, in their suspended condition, have only small feed windows around the inserts for inserting pipets into the well.

Patent document U.S. Pat. No. 4,871,674 describes that the cell culture insert can be moved into an upper position to enlarge the feed window for inserting a pipet. In the process, the cell culture insert rests against the wall of the well, resulting in the cells in the well being damaged.

Furthermore, from U.S. Pat. No. 5,272,083, a cell culture insert is known that carries on an upper flange a support arm arrangement, which conically narrows by less than 45 degrees until it reaches a cylindrical culture chamber, with cutouts being provided between the support arms that provide pipet accessibility. The culture chamber in this case is significantly constricted, to approximately ¼ of the diameter of the receiving space.

The known cell culture inserts are produced either of a completely colorless transparent material or of the same single-color plastic as the cell culture plate with the wells. This makes it difficult to differentiate between the well and the cell culture insert, thus rendering manual or automated work more difficult.

It is the object of the invention to provide an improved cell culture insert with a sufficiently large membrane surface in which the feed window for the well is significantly larger and in which no moving of the insert is required to insert pipets into the feed window.

This object is met in such a way that the spacers around the circumference of the cell culture insert are distributed in such a way, and implemented with different lengths to the side in such a way, that one large feed window and multiple smaller windows are created.

Advantageous embodiments of the invention are specified in the subclaims.

The beaker-shaped cell culture insert hangs from support arms on the upper edge of the well and is positioned asymmetrically by means of spacers having different lengths. In the process, a feed window, into which pipets can comfortably be inserted, is created between the longest spacers.

Three spacers, which are distributed around the circumference over more than half the circumference are required as a minimum to position the cell culture insert in the well opening in a defined manner. The largest feed window is created if one of the three spacers is shorter than the other two.

This arrangement has the advantage that the shortest spacer determines a minimum space between the cell culture insert and the wall of the well in such a way that capillary narrow spaces of cells between the cell culture insert and the wall of the well are prevented, so that no liquid rises there.

Advantageously, one short spacer and two spacing webs of equal length are arranged equally spaced around the circumference of the beaker. The spacing webs which, when the cell culture insert is inserted into the well, perform an asymmetrical positioning therein, are advantageously downwardly tapered. The support arms ensure that the cell culture insert is suspended in the well at a defined elevation. The shortest spacer ensures that a minimum space is maintained between the walls of the cell culture insert and the well.

In a particularly advantageous embodiment at least one wall cutout, which is provided in the insert wall at its upper end between the long spacers, creates further improved accessibility for pipets. The depth of the cutout is approximately 20% of the height of the insert. The lower edge of the wall cutout has an adequate safe distance to the liquid culture medium. To prevent critical bending stresses, the cutout edge extends upwardly diverging and rounded toward the support arms. The insert wall has a relatively large diameter in the culture chamber since it is provided only with shaping inclines of approximately 1.5 degrees on the outside and 3.3 degrees on the inside. As a result, the free membrane diameter is larger than the radius of the well. If wall cutouts are provided between all support arms, not only the pipet accessibility is significantly enhanced, but also the tweezer access to the support arms.

Despite the eccentric suspension of the cell culture insert in the well, a sufficiently large observation window of, e.g., 3 mm diameter remains over the center of the well for the automated optical evaluation of the cell culture plates with the above described cell culture inserts.

If a larger feed window is required, the cell culture insert can be pushed up with a pipet in such a way that it can slide a short distance out of the well along the inclined spacers. After removing the pipet, the cell culture insert reliably slides back into the well along the spacers. The high enclosed construction of the cell culture insert prevents a contamination between the inside and outside of the cell culture insert.

For handling the cell culture insert in the well, it can easily be grasped on one of the long support arms, inserted, and also lifted back out, with the aid of a pair of tweezers.

Any known membrane for cell culture inserts may be used; capillary membranes of polyester or polycarbonate have the advantage of a precisely adjustable porosity and transparency.

The cell culture insert is advantageously produced of a tinted plastic that represents a visible contrast to the material of the well. This improves the recognizability of the feed opening. Preferably a transparent colored plastic will be used.

An embodiment of the invention is described in the figures by way of example.

FIG. 1 shows a top view of a cell culture insert of a first embodiment in the well, FIG. 2 shows a view of the cell culture insert from the side with three spacing webs, FIG. 3 shows a view of the cell culture insert from the side with spacing webs and spacer, FIG. 4 shows a sectional view of the well with cell culture insert with spacer, FIG. 5 shows a sectional view of the well with cell culture insert with inclined wall, FIG. 6 shows a second embodiment of the insert in the perspective;

Figure 1:
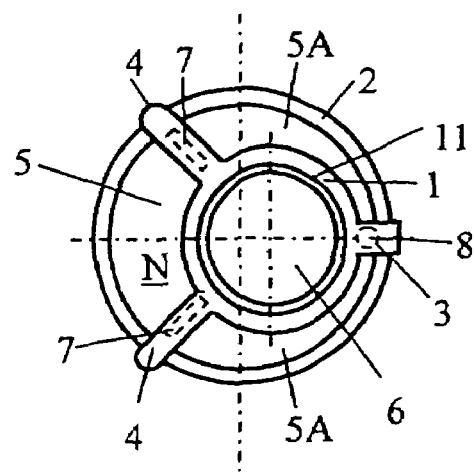

FIG. 1 shows a cell culture insert 1 of a first embodiment in a top view, showing how in a round opening in the well 2, a cell culture insert 1 is held eccentric to the opening. It is held by three support arms 3, 4, wherein the support arm 3 is implemented shorter than the other two. This creates a large feed window 5, into which a pipet can easily be inserted, as well as two smaller windows 5A. The opening 6 of the cell culture insert is also easily accessible from above. The support arms 3, 4, each are arranged offset by 120 degrees. The eccentricity between the axis of the well and that of the insert is more than 1.3 mm, e.g., 4 mm. It is achieved by means of different spacing webs that are arranged below the support arms 3, 4.

Figure 2:
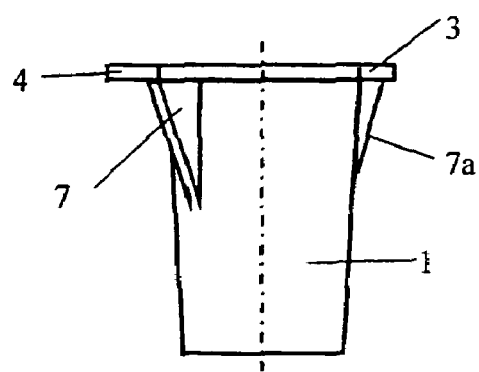

FIG. 2 shows a side view of the beaker-shaped cell culture insert 1. On it, long triangular spacing webs 7 are affixed laterally, tapering downward, and another shorter spacing web 7a. At the top, the support arms 3, 4, are formed on the insert wall 11, of which the support arm 3 is shorter, which belongs to the shorter spacing web 7a.

Figure 3:
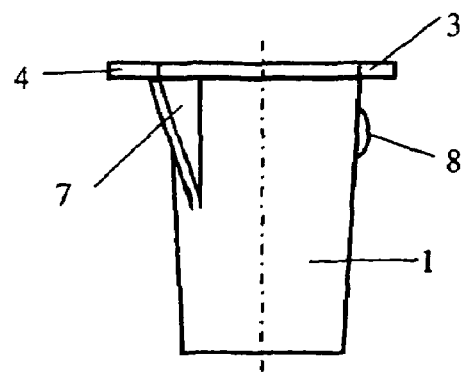

FIG. 3 shows a side view of the beaker-shaped cell culture insert 1 in a modified design. On it, the triangular spacing webs 7 and another spacer 8 in knob-shape are affixed.

Figure 4:
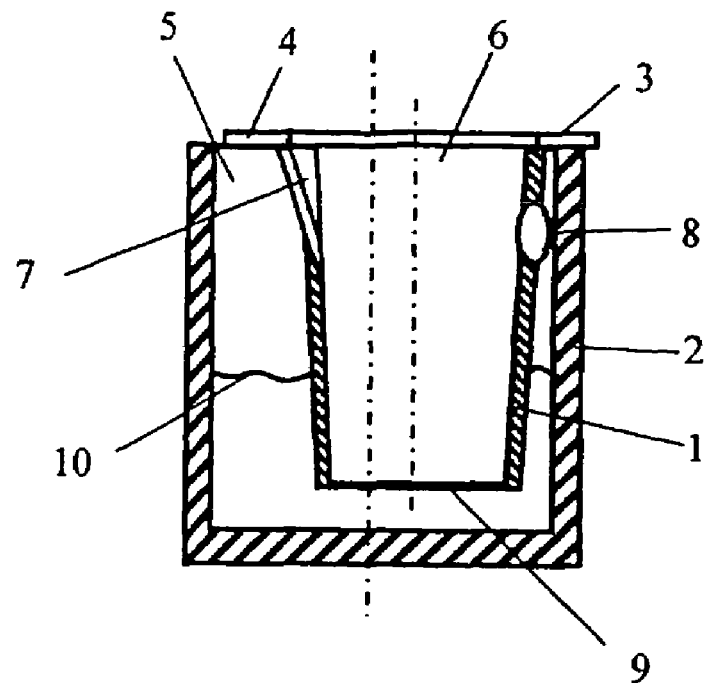

FIG. 4 shows a section through the cylindrical well 2 with suspended cell culture insert 1. The support arms 3, 4 rest on the top of the well 2 and determine the elevation of the cell culture insert 1. Via the spacing webs 7 and the spacer 8, the space between the walls is maintained in a defined manner. The feed window 5 is located between the long support arms 4. The cell culture insert 1 has at its top the opening 6 and at its bottom the membrane 9. The space between the walls at the level P of the fluid surface 10 is sufficiently large so that no capillary effect occurs.

Figure 5:
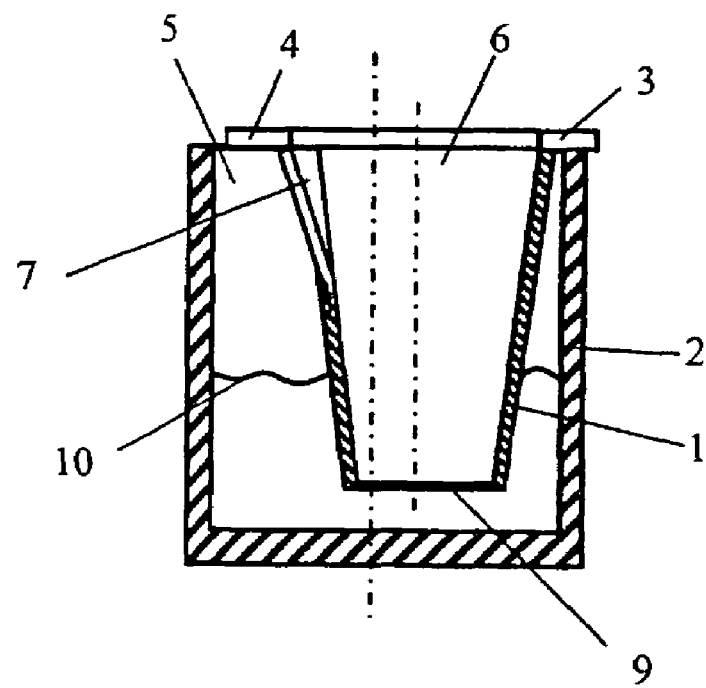

FIG. 5 shows the same section as FIG. 4, with the difference that the space between the walls of the insert 1 and well 2 at the height of the fluid surface 10 is determined by the relatively greater incline of the cell culture insert 1, which is approximately 7 degrees in the example.

Figure 6:
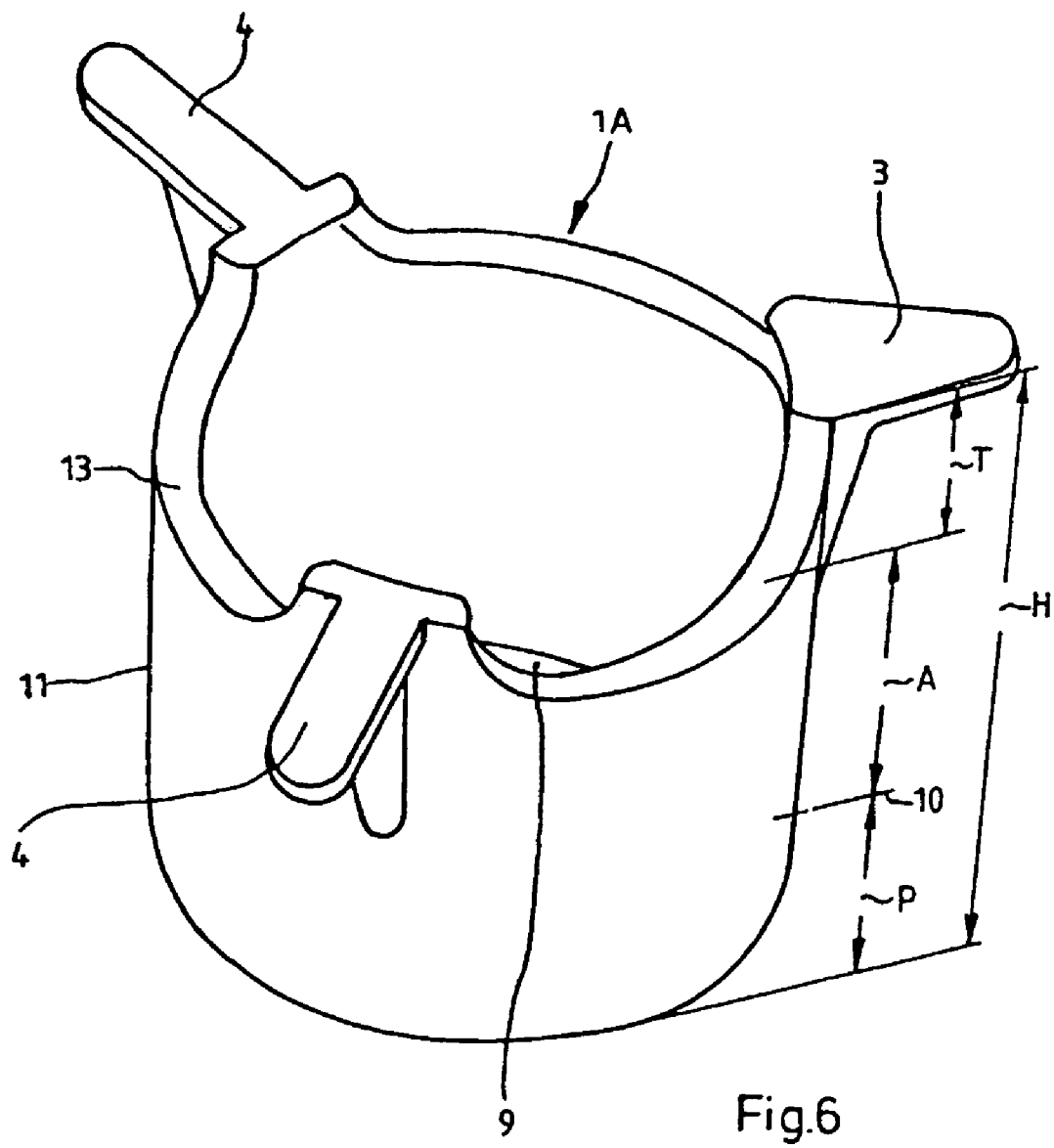

FIG. 6 shows, in the perspective, an additional embodiment of a cell culture insert 1A, wherein the insert wall 11 has a wall cutout 12 from the top between the support arms 3, 4 in each case that is designed rounded toward the support arms. The cutout depth T is approximately 20% of the insert height H, so that the lower edge 13 of the wall cutouts 12 has a sufficient level distance H to the normal fluid surface 10.

Figure 7:
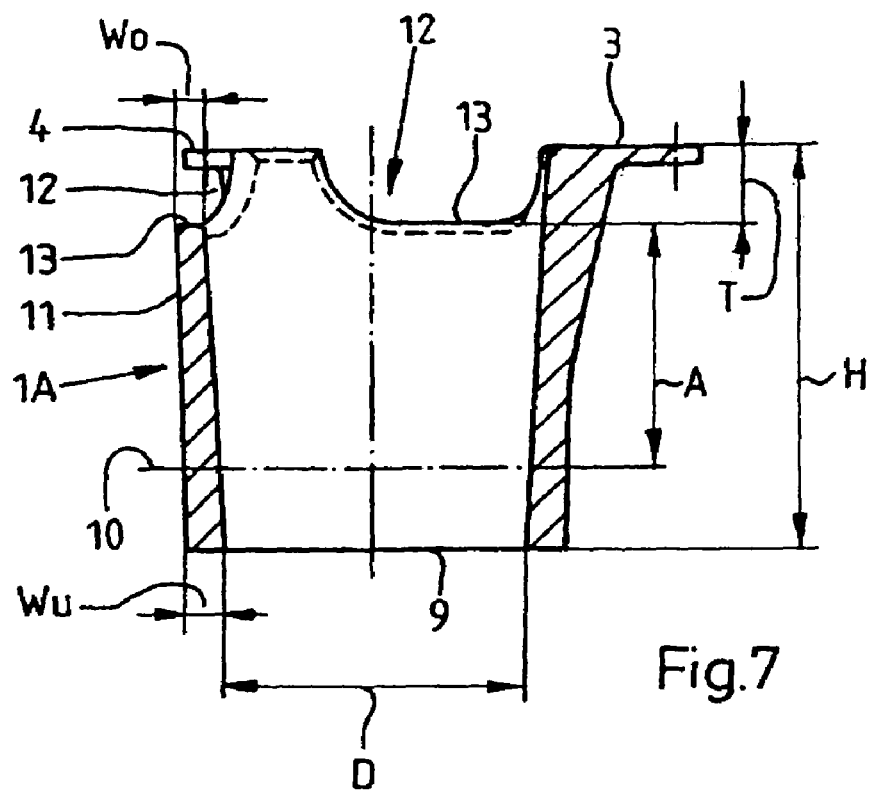
FIG. 7 shows an axial section A-A for the above.

FIG. 7 shows an axial cross section through the embodiment in FIG. 6. In the figure, the size ratio of the cutout depth T to the insert height H is apparent, the latter being approximately five times larger. The normal level P of the liquid culture medium 10 is also shown, which is located approximately ⅓ of the insert height H above the membrane 9. The insert wall 11 is conically narrowed on its outside with a shaping incline of approximately 1.5 degrees and tapered on its inside with approximately 3.3 degrees so that the upper wall thickness WO increases toward the bottom from 1 mm to a lower wall thickness WU of 1.5 mm, thus creating a secure sealing edge at the bottom for the membrane 9 and more circumferential free space at the top.

Figure 8:
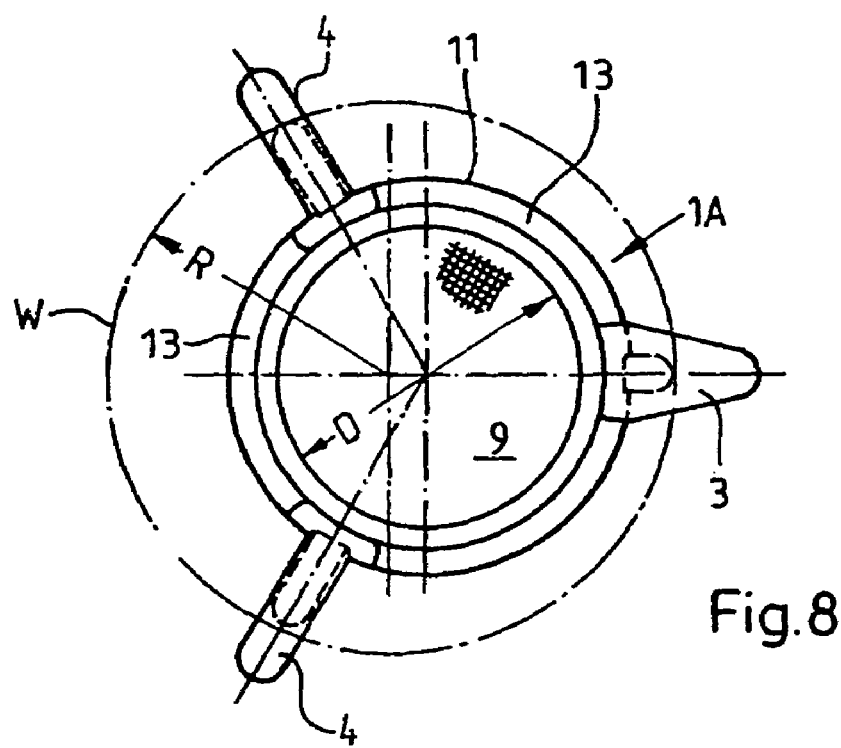
FIG. 8 shows a top view for the above.

FIG. 8 shows a top view of FIG. 7. The interior wall W of the well has been marked with a dot-and-dash line, the well radius R of which is smaller than the membrane diameter D. The eccentricity of the insert 1a to the interior well wall W is approximately 1.5 mm in the example. The well radius R is 10-12 mm, for example, and the usable diameter D of the membrane 9 is 11-13 mm. The insert wall 11 is approximately 15-17 mm wide at the top. The spacers 7, 8, through their different lateral extension, create an eccentricity of the insert 1A in the well 2 of 1.3-1.7 mm.

List of Reference Numerals

1A Cell culture insert
2 Well
3 Short support arm
4 Long support arm
5 Feed window, large
5a Feed window, small
6 Opening of the cell culture insert
7 Long spacing web
7a Short spacing web
8 Spacer
9 Membrane
10 Fluid surface
11 Insert wall
12 Wall cutout
13 Lower edge of the wall cutout
A Level distance to the lower edge
D Membrane diameter
H Insert height
N Liquid culture medium
P Level
R Well radius
T Cutout depth
W Interior well wall
WO Upper wall thickness
WU Lower wall thickness

What is claimed is:

1. A cell culture insert (1) comprising a beaker-shaped insert wall (11) having a membrane filter bottom (9), a top, and projecting support arms (3, 4) that are distributed around the circumference of the top and having lateral spacers (7, 8) for a vertical and horizontal orientation in a well (2) with a liquid culture medium (N) in a cell culture plate, characterized in that the spacers (7, 8) are distributed around the circumference of the cell culture insert (1) and have different lengths to the insert wall (11) including a shortest spacer (8), in such a way that one large feed window (5) and multiple smaller windows (5A) are created when the insert (1) is in rest position in the well (2); wherein the shortest spacer (8) has a knob shape.

2. A cell culture insert according to claim 1, characterized in that at least two of the spacers (7) are constructed as triangular spacing webs that are tapered towards the bottom.

3. A cell culture insert according to claim 1, characterized in that the shortest spacer (8) determines a minimum space between the insert wall (11) of the cell culture insert (1) and the interior wall (W) of the well (2), which prevents a capillary rising of the liquid culture medium (N).

4. A cell culture insert according to claim 1, characterized in that the space between the insert wall (11) of the cell culture insert (1) and an interior wall (W) of the well (2) is determined by the height of the knob shaped spacer (8).

5. A cell culture insert according to claim 1, characterized in that the cell culture insert (1) is held on three support arms (3, 4) eccentrically suspended in the well (2).

6. A cell culture insert according to claim 5, characterized in that the support arms (3, 4) are arranged adjoining above the spacers (7, 8) and offset around the circumference by 120 degrees in each case.

7. A cell culture insert according to claim 1, characterized in that the insert wall (11) incorporates at the top, at least between the two longer support arms (4), a wall cutout (12)

having a lower edge (13) that is located at a distance above a normal fluid surface (10) of the liquid culture medium (N).

8. A cell culture insert according to claim 7, characterized in that the lower edge (13) of the wall cutout (12) extends to the support arms (3, 4) in an arc shape.

9. A cell culture insert according to claim 7, characterized in that the wall cutout has a depth (T) that is approximately 20% of an insert elevation (H) of the insert (1, 1A).

10. A cell culture insert according to claim 1, characterized in that its insert wall (11) has, at its end facing the membrane, a greater wall thickness (WU) than at the top.

11. A cell culture insert according to claim 10, characterized in that its insert wall (11) is tapered on the outside from the top toward the bottom with a shaping incline of approximately 1.5 degrees and that the insert wall (11) has on its inside an incline of 3.3 degrees.

12. A cell culture insert according to claim 11, characterized in that the membrane (9) has a diameter (D) larger than an inner well radius (R) of the surrounding well (2).

13. A cell culture insert according to claim 11, characterized in that the well radius (R) is 10-12 mm, the diameter (D) of the membrane (9) is 11-13 mm, the insert wall is 15-17 mm wide on the outside at the top and the spacers (7, 8) ensure an eccentricity of over 1.3 mm of the cell culture insert (1) relative to the well (2).

14. A cell culture insert according to claim 1, characterized in that it is composed of tinted material.

15. A cell culture insert according to claim 14, characterized in that it is composed of transparent material.

16. A cell culture insert (1) comprising a beaker-shaped insert wall (11) having a top, a membrane filter bottom (9) and projecting support arms(3, 4) distributed around the circumference of the top of the insert, and having lateral spacers (7, 8) for vertical and horizontal orientation of the cell culture insert (1) in a well (2) containing a liquid culture medium (N) in a cell culture plate, wherein lateral spacer (8) is knob shaped;

wherein at least one of said projecting support arms (3, 4) is shorter than at least one other (4) of said projecting support arms (3, 4), whereby the cell culture insert (1) in rest position is eccentrically suspended in the well (2) by the support arms (3, 4) so that one large feed window (5) and a plurality of smaller windows (5A) are created.

\* \* \* \* \*